(12) United States Patent
Eger et al.

(10) Patent No.: US 8,397,720 B2
(45) Date of Patent: Mar. 19, 2013

(54) RESPIRATOR AND A PROCESS FOR OPERATING A RESPIRATOR

(75) Inventors: Marcus Eger, Lübeck (DE); Dieter Weismann, Groß Grönau (DE)

(73) Assignee: Dräger Medical GmbH, Lübeck (DE)

( * ) Notice: Subject to any disclaimer, the term of this patent is extended or adjusted under 35 U.S.C. 154(b) by 1358 days.

(21) Appl. No.: 12/112,485

(22) Filed: Apr. 30, 2008

(65) Prior Publication Data
US 2009/0020119 A1   Jan. 22, 2009

(30) Foreign Application Priority Data
Jul. 19, 2007   (DE) .......................... 10 2007 033 546

(51) Int. Cl.
*F16K 31/02* (2006.01)
*A61M 16/00* (2006.01)

(52) U.S. Cl. .......... 128/204.21; 128/204.18; 128/200.24

(58) Field of Classification Search ............. 128/200.24, 128/204.18, 204.21, 204.23
See application file for complete search history.

(56) References Cited

U.S. PATENT DOCUMENTS

| | | | | |
|---|---|---|---|---|
| 4,972,842 A | * | 11/1990 | Korten et al. | 600/529 |
| 5,261,397 A | * | 11/1993 | Grunstein | 128/204.18 |
| 5,540,220 A | * | 7/1996 | Gropper et al. | 128/204.23 |
| 5,884,622 A | * | 3/1999 | Younes | 128/204.21 |
| 6,532,959 B1 | * | 3/2003 | Berthon-Jones | 128/204.23 |
| 8,109,269 B2 | * | 2/2012 | Eger | 128/204.23 |

* cited by examiner

*Primary Examiner* — Annette Dixon
(74) *Attorney, Agent, or Firm* — McGlew and Tuttle, P.C.

(57) ABSTRACT

Operating a respirator with an inspiration pressure-vs.-time curve (1), which has an airway target pressure ($p_{aw\_target}$) and a PEEP (3), in which the inspiration pressure-vs.-time curve (1) reaches the airway target pressure ($p_{aw\_target}$) on a ramp-like curve (17) starting from a starting airway pressure ($p_{aw\_Start}$), which is greater than the PEEP (3).

20 Claims, 7 Drawing Sheets

RESPIRATOR AND A PROCESS FOR OPERATING A RESPIRATOR

CROSS REFERENCE TO RELATED APPLICATIONS

This application claims the benefit of priority under 35 U.S.C. §119 of DE 10 2007 033 546 filed 19/Jul./2007, the entire contents of which are incorporated herein by reference.

FIELD OF THE INVENTION

The present invention pertains to a process for operating a respirator (also known as a ventilator) where breathing gas is supplied according to an inspiration pressure-vs.-time curve. The pressure/time curve has an airway target (end) pressure and a PEEP (positive end-expiratory pressure). The present invention pertains, furthermore, to a respirator supplying breathing gas according to an inspiration pressure-vs.-time curve, where the pressure/time curve has an airway target (end) pressure and a PEEP (positive end-expiratory pressure).

BACKGROUND OF THE INVENTION

It is not yet possible in case of the pressure-supported or pressure-controlled respiration (also known as a ventilation) of patients to automatically adapt the changes in the respiration pressure over time as well as the duration of the inspiration breathing stroke to the individual breathing mechanics of the patient and especially to the patient's lung diseases or limitations.

Such an adaptation to the patient's clinical picture would, however, be desirable, because the breathing or lung mechanics of, e.g., a patient with Chronic Obstructive Pulmonary Disease (COPD) differs from that of a patient with Acute Respiratory Distress Syndrome (ARDS), which also affects the optimal mechanical respiration. For example, the compliance of a patient with COPD is comparatively high, whereas patients with ARDS have a comparatively low compliance.

It is advantageous for COPD patients to be respirated with an initially high airway pressure and with a comparatively low pressure at a later stage of the inspiration to overcome resistive resistances. These patients require a time that is above average for the expiration. To guarantee sufficient expiration during passive breathing out, the duration of inspiration is therefore selected to be usually short and the inspiration pressure to be high (see FIGS. 1 and 2). If excessively long inspiration times are selected, overinflation of the lungs may, however, occur, especially in case of respiration with pressure support and/or a flow-based cycle-off criterion selected as an excessively insensitive criterion. Moreover, asynchronous patient activity, which counteracts the relaxation of the muscles and facilitates the build-up of a PEEP, is often facilitated. This is disadvantageous for the patient.

Contrary to this, ARDS patients must be respirated cautiously with high pressures in order to achieve a sufficient gas exchange. The necessary pressure is usually increased gradually to the maximum inspiration pressure. By contrast, comparatively little time is needed for the expiration, because the strong elastic resetting forces help expel the gas volume breathed in rapidly. Short expiration times are therefore regularly selected, also increased to prevent recruited lung areas from collapsing by achieving an intended intrinsic PEEP. However, the respiration of ARDS patients leads, especially when the flow-based cycle-off criterion common in case of pressure support is used, to very short inspiration times and to a patient activity that is asynchronous in relation to the respiration pattern, as this can be seen in FIG. 3.

SUMMARY OF THE INVENTION

The object of the present invention is therefore to propose a process for operating a respirator, which makes possible the improved respiration of patients, especially with different lung diseases, compared to the state of the art. Another object of the present invention is to propose a suitable device.

The object according to the present invention is accomplished by recording a PEEP (positive end-expiratory pressure) of the patient, providing an inspiration pressure/time curve, and flowing breathing gas into the patient according to the inspiration pressure/time curve. The pressure/time curve transitions from a starting airway pressure at a beginning of an inspiration stroke to an airway target pressure at an end of the inspiration stoke, where the starting airway pressure is higher than the PEEP.

Thus, a process for operating a respirator with an inspiration pressure-vs.-time curve, which has an airway target pressure and a PEEP (positive end-expiratory pressure), is proposed according to the present invention. In the process according to the present invention, the inspiration pressure-vs.-time curve reaches the airway target pressure according to a ramp-like curve starting from a starting airway pressure, which is greater than the PEEP.

A respirator is defined according to the present invention as any device that is used to respirate and/or anesthetize a human or animal patient.

A ramp-like pressure curve is defined in the sense of the present invention as a deviation from the rectangular or approximately rectangular pressure curve known from practice in case of mechanically supported inspiration. In other words, a ramp-like curve (hereinafter also called "ramp" for short) is defined as a deviation especially at the beginning of a mechanical inspiration stroke, by means of which adaptation of the inspiration pressure curve to the individual pulmonary conditions of a patient is performed. The term "ramp" should not therefore be understood exclusively to be a rise from one pressure level to a higher pressure level; a ramp may also mean a drop in pressure from a higher to a lower pressure level. The graphic shape of a ramp in the sense of the present invention is not limited here to a linear, stepped, exponential curve or a curve having another shape. The term "ramp" is also replaced by "pressure switching" to describe the present invention. This pressure switching may be both positive, i.e., mean a rise in pressure, and negative, i.e., mean a drop in pressure.

One advantage that can be gained by means of the process according to the present invention is that adaptation to the patient and to a possibly present lung disease is possible by approximating the respiration pressure from a starting airway pressure to the desired airway target pressure by means of a ramp-like pressure curve, which approximation is proposed according to the present invention. When using the process according to the present invention, it is therefore possible in case of pressure-supported or pressure-controlled respiration of the patient to carry out respiration adapted to the patient's lung disease.

Advantageous variants of the solution according to the present invention are the subject of the subclaims.

Thus, it is proposed in an advantageous embodiment that not only a lung disease, but also the entire past pulmonary history and/or the entire pulmonary status be taken into account during respiration.

While the taking into account of a lung disease can already be taken into account in the present invention in the above-described, in the most general form thereof, by entering the information on the respirator that this or that particular disease is present and the ramp-like pressure curve and by selecting corresponding to experience that has proved to be helpful in connection with the respiration of a large number of patients with the same disease, the ramp-like pressure curve is set in this embodiment on the basis of the pulmonary status that is present in the individual patient. Possibilities of the technical implementation will be described in detail below. One advantage associated with this embodiment of the present invention is the more widely individualized respiration of the patient as well as the advantages already known to the person skilled in the art.

It is proposed in another preferred embodiment that a desired time constant, which indicates a desired dynamics of filling of the lungs over time, be set during the treatment or the respiration of the patient. This desired time constant can be set on the device by the physician, but it may also be stored in the respirator operated with the process according to the present invention.

Furthermore, the desired time constant can be rated for different clinical pictures of a patient to be respirated. A desired time constant, which is especially suitable for a certain lung disease, and which is based, for example, on empirical values from previous respirations of the same patient or of other patients, may be stored in the device, so that it may suffice, before the beginning of the respiration of the patient, to know what lung disease is present in the patient. It may therefore suffice to indicate the type of the pulmonary impairment on the respirator or on a means intended for this purpose.

In a next step of this embodiment, a time constant of the lung mechanics of the patient is determined or estimated in the process according to the present invention. This time constant of the lung mechanics can, moreover, also be found in tables or set on the device for different lung diseases. Thus, a time constant of 0.1 sec of the lung mechanics can be set or may be able to be set for an ARDS patient, 1.0 sec for a COPD patient, and 0.3 sec for a patient having unremarkable pulmonary conditions. This time constant should reflect—if possible and necessary—the actually prevailing conditions of the lung mechanics. It offers a clue as to the extent to which the respiration pressure must be adapted to the existing circumstances in order to implement the desired time constant during the respiration.

The process according to the present invention provides, furthermore, for calculating the ramp-like pressure curve in this embodiment. The ramp-like pressure curve or the pressure switching at each time t, as the ramp-like pressure curve is also called in connection with this invention, can be calculated during the inspiration, for example, according to formula (1).

$$\Delta p_{aw} = [p_{aw\_Start} - p_{aw\_target}] \cdot e^{-\frac{t}{\tau_{desired}}} \quad (1)$$

If a certain dynamics of filling of the lungs over time shall be preset, $$p_{aw\_Start} = p_{aw\_target} \cdot \frac{\tau}{\tau_{desired}} \quad (2)$$

can be written for the starting airway pressure $p_{aw\_Start}$.

Thus, $$\Delta p_{aw} = p_{aw\_target} \cdot \left[\frac{\tau}{\tau_{desired}} - 1\right] \cdot e^{-\frac{t}{\tau_{desired}}} \quad (3)$$

is obtained for the pressure switching $\Delta p_{aw}$.

Formulas (1) and (3) can be approximated, e.g., linearly (interruption of the power series expansion of the e function according to the first term), so that $$\Delta p_{aw} = [p_{aw\_Start} - p_{aw\_target}] \cdot \left[1 - \frac{t}{\tau_{desired}}\right] \quad (4)$$

and $$\Delta p_{aw} = p_{aw\_target} \cdot \left[\frac{\tau}{\tau_{desired}} - 1\right] \cdot \left[1 - \frac{t}{\tau_{desired}}\right] \quad (5)$$

are obtained.

Formulas (4) and (5) are valid for $0 \leq t \leq \tau_{desired}$. If t is in another range, the pressure switching $\Delta p_{aw}$ assumes the value 0. A linear ramp, which begins, however, at a pressure above PEEP, is obtained due to the linearly approximated pressure switching $\Delta p_{aw}$.

To determine the time constant of the patient's lung mechanics, it is proposed that it be determined in another preferred embodiment by means of the regression method and/or the occlusion method. However, it is also possible to use other methods, which are not being mentioned here, and which are known to the person skilled in the art but have not yet been used so far in the context according to the present invention. Reference is made in this connection to the relevant literature. However, the time constant of the lung mechanics can also be set on the respirator or on a means intended for this purpose, as it is proposed in another preferred embodiment. This is especially beneficial if, for example, the time constant of the lung mechanics is already known for one and the same patient from past determinations or determinations carried out in the meantime or from investigations carried out independently from the respiration.

It is apparent from the above discussion that the determination of the time constant of the lung mechanics can be determined once at the beginning of a respiration or several times in the course of a respiration. The latter is especially advantageous when the time constant of the patient's lung mechanics usually changes or at least can be changed based on repositioning of the patient in connection with a surgery or after transfer into another bed. Regardless of the presence of additional features, automatic determination of the time constant of the lung mechanics can be provided for in each embodiment according to the present invention. This has the advantage that a necessary or reasonable pressure switching can be determined without any additional activity on the part of a physician or the patient's caregiver.

Another embodiment, which is likewise preferred, comprises the step of setting the starting airway pressure, the setting of a time constant for determining the change in the inspiration pressure applied and of the calculation of the ramp-like pressure curve, which was already discussed above. The statement or the setting of the starting airway pressure and the setting of a time constant, which indicates the rate at which the inspiration pressure applied changes, makes it possible to calculate the ramp-like pressure curve in an alternative manner. Knowledge of the time constant of the respiration mechanics of the lungs is not necessary for this, unlike in the exemplary embodiment discussed above. The ramp-like pressure curve over time between the starting airway pressure and the airway target pressure can be determined, for example, corresponding to the formulas (1) or (4) presented above.

The object according to the present invention is also accomplished by a respirator performing the above process.

Since all the advantages discussed above can be gained to the full extent with the device according to the present invention, reference is explicitly made here to the discussion of these advantages to avoid repetitions.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
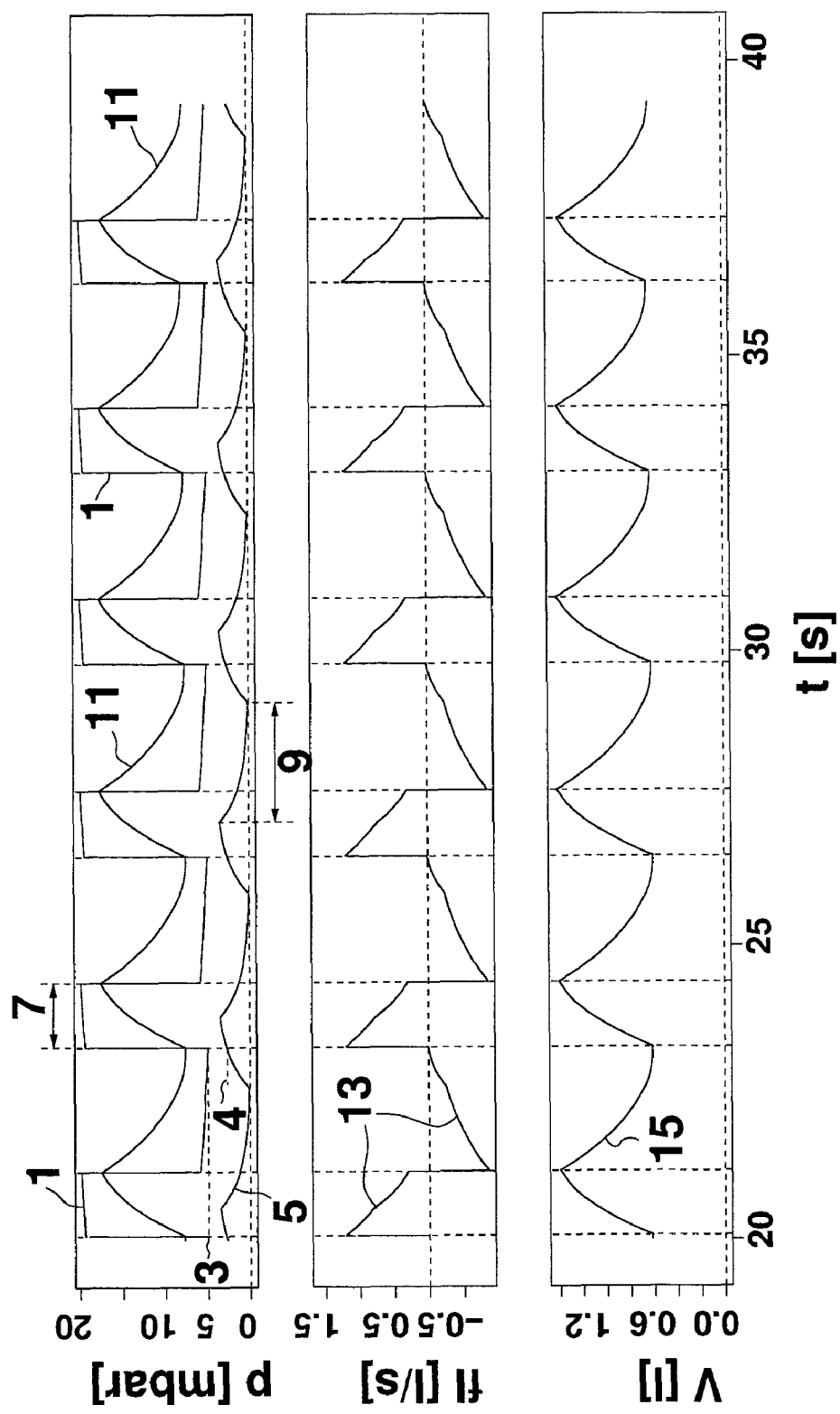
FIG. 1 is a plurality of graphs showing a simulation of the pressure-supported respiration of a COPD patient.

Referring to the drawings in particular, FIG. 1 shows a simulation of the pressure-supported respiration of a COPD patient with average compliance, high resistance and an inspiration pressure curve 1, as it is usually applied in practice.

The high intrinsic PEEP (positive end-expiratory pressure) 4 shown in the upper graph representation in FIG. 1, in which the curve of the respiration pressure or inspiration pressure above PEEP 3 is shown, requires [DA1] a high muscle activity 5, which is shown as the lowermost curve in the upper representation in FIG. 1, in order to trigger the respective next triggered breathing stroke. The mechanical inspiration time 7 reaches far into the expiration phase 9 of the patient. FIG. 1 shows, furthermore, the pressure 11 prevailing in the lungs. The graph representation in the center in FIG. 1 shows the patient flow or flow 13 over time. The graph representation at the bottom in FIG. 1 shows the gas volume 15 within the lungs over time.

Figure 2:
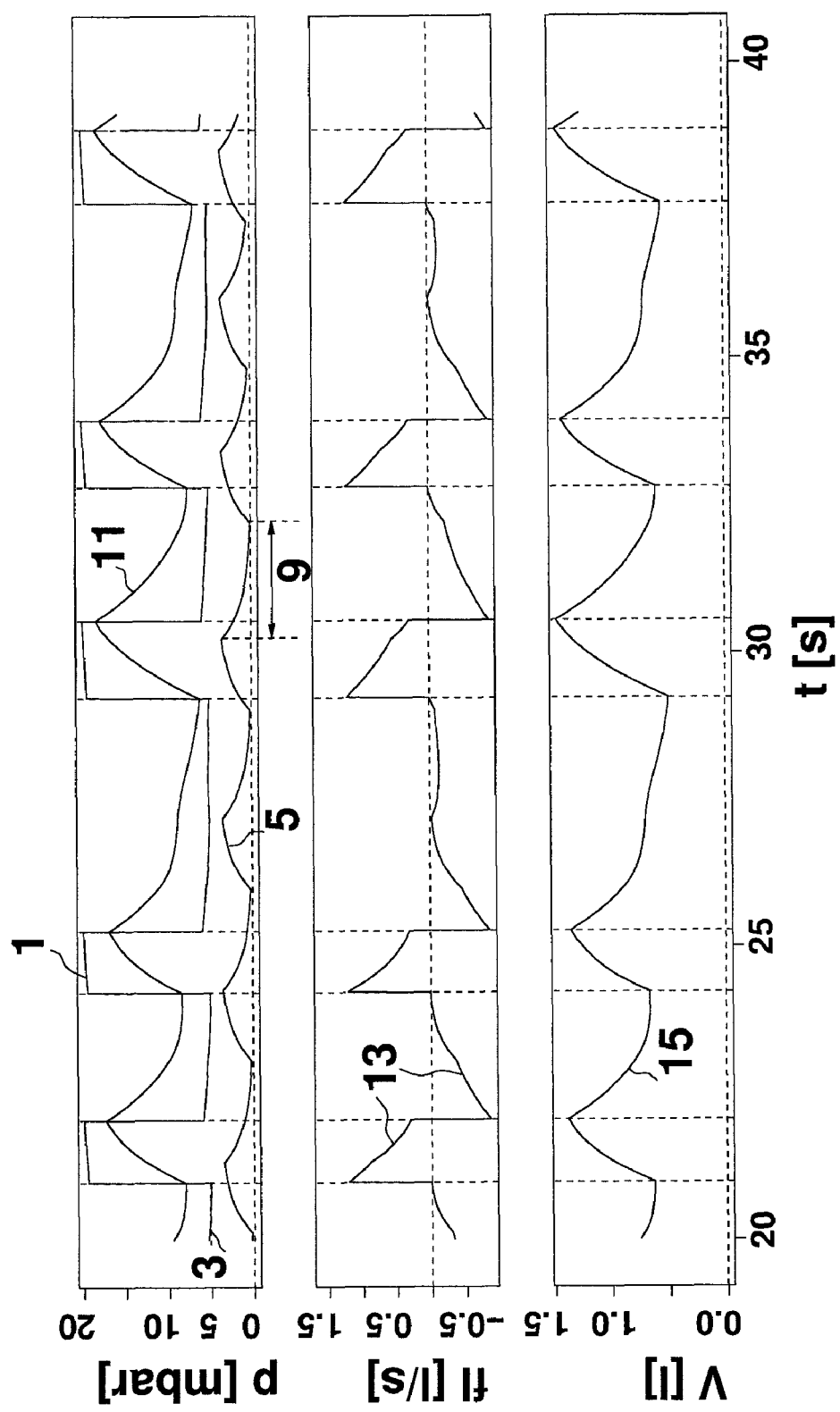
FIG. 2 is a plurality of graphs showing a simulation as in FIG. 1 with desynchronization between the respirator and the patient.

FIG. 2 shows a simulation as in FIG. 1, where it can be recognized in FIG. 2 that a great desynchronization develops between the respirator and the patient and a so-called "missing trigger" develops. Both the simulation according to FIG. 1 and that according to FIG. 2 was carried out with the parameter values compliance C=80 mL/mbar and resistance R=12 mbar/(L/sec).

Figure 3:
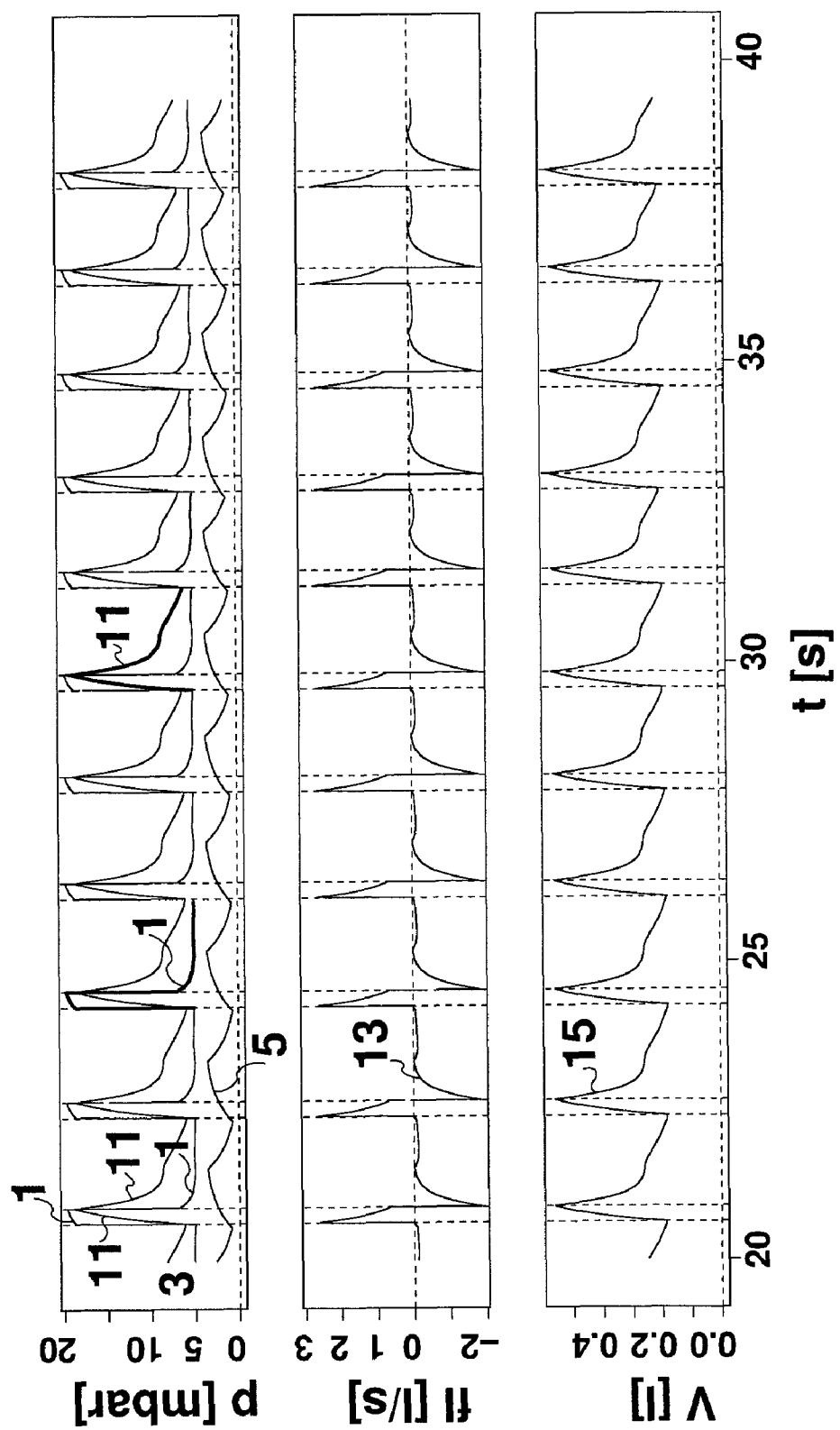
FIG. 3 is a plurality of graphs showing a simulation of the pressure-supported respiration of an ARDS patient.

FIG. 3 shows a simulation with C=30 mL/mbar and R=5 mbar/(L/sec) of a pressure-supported respiration of an ARDS patient with low compliance and average resistance. The inspiration times obtained are very short due to the flow-based cycle-off criterion for the changeover from inspiration to expiration, which criterion is common in case of pressure support.

Figure 4:
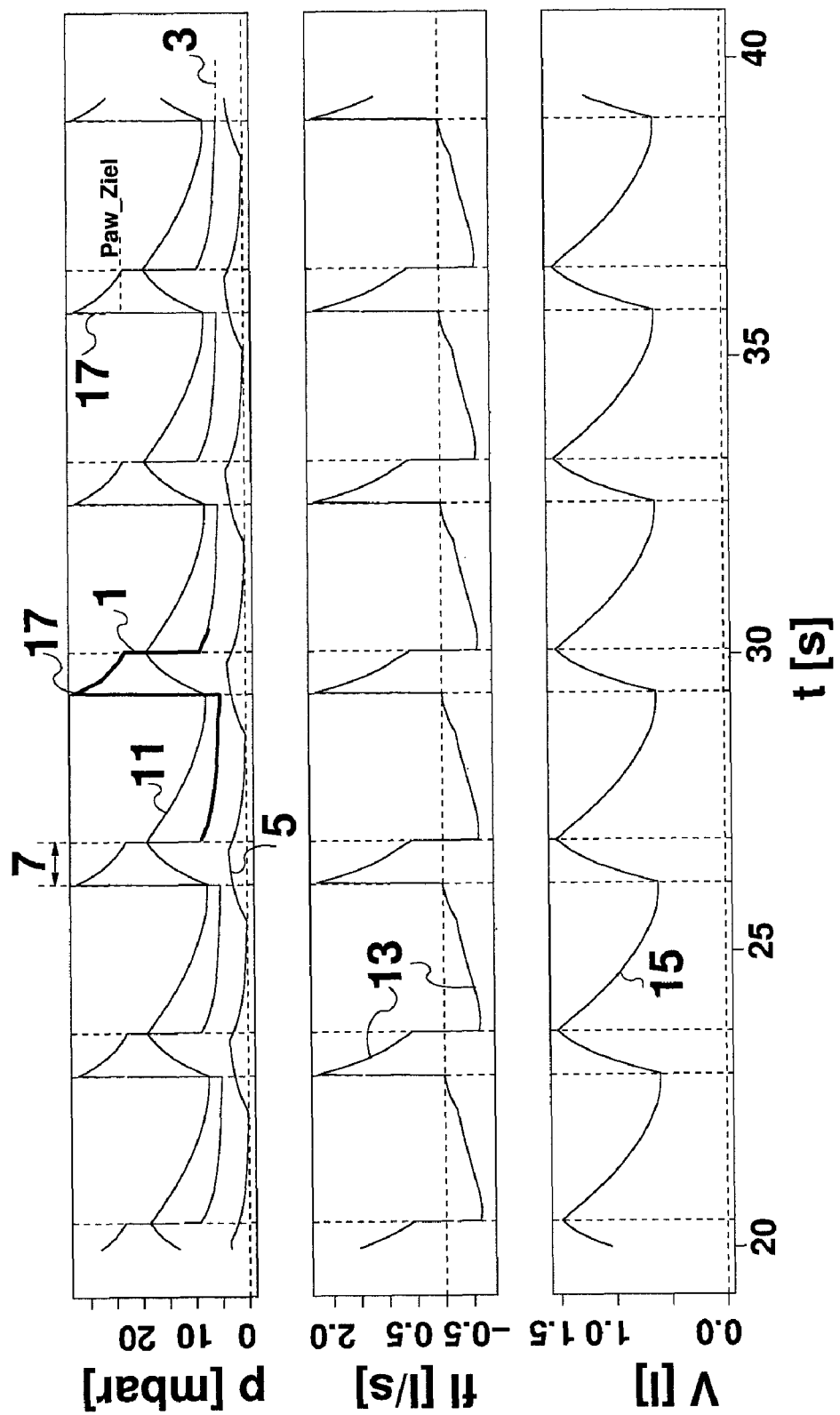
FIG. 4 is a plurality of graphs showing a simulation of the pressure-supported respiration of a COPD patient as in FIG. 1, but with the use of the process according to the present invention.

FIG. 4 shows a simulation of the pressure-supported respiration of a COPD patient, as in FIG. 1, which simulation is run with the values given above for C and R for FIGS. 1 and 2, but with the use of the inspiratory pressure switching according to formula (3), where $\tau_{desired}$=0.5 sec was selected. The inspiration time thus becomes considerably shorter, so that more time is left for the expiration, and the intrinsic PEEP can advantageously decrease. An increase in the initial inspiration pressure (here pressure switching 17), which can be recognized compared to the same representation in FIG. 1, can be recognized in the inspiration cycle marked in bold. This ramp-like increase (or pressure switching 17) advantageously makes it possible to respirate the COPD patient with a temporarily higher pressure at the beginning of the inspiration and to gain hereby the advantages mentioned above, before the pressure drops to the airway target pressure $p_{aw\_target}$. It can be recognized compared to the respective representations in the top parts of FIGS. 1 and 4 that the inspiration time is advantageously shortened in case of the use of the process according to the present invention, as in FIG. 4, and the mechanical inspiration time 7 no longer reaches appreciably into the patient's expiration phase.

Figure 5:
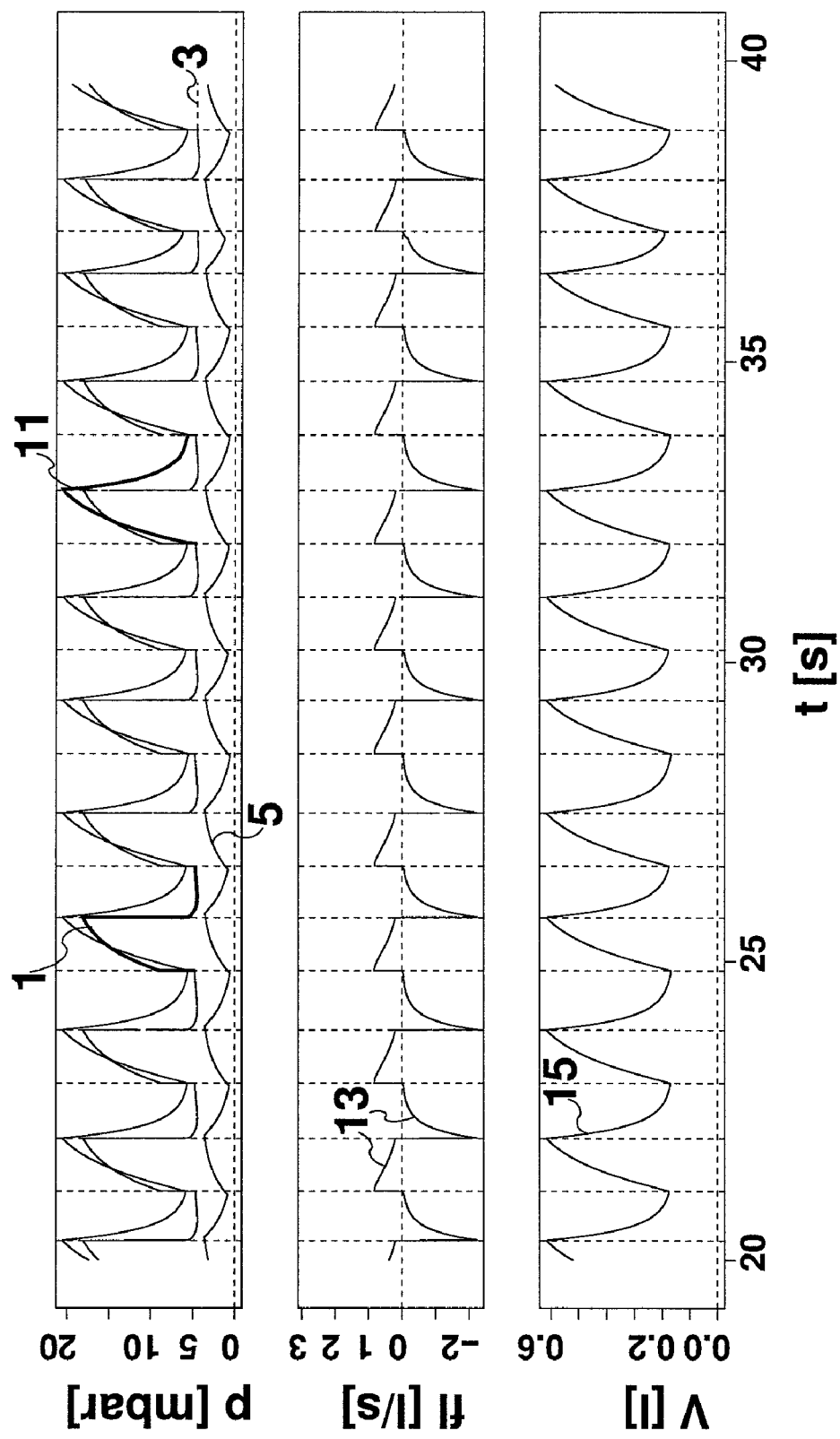
FIG. 5 is a plurality of graphs showing a simulation of the pressure-supported respiration of an ARDS patient as in FIG. 3, but with the use of the process according to the present invention.

FIG. 5 shows the situation of the pressure-supported respiration of an ARDS patient as in FIG. 3, but with the use of the inspiratory pressure switching according to formula (3), where $\tau_{desired}$=0.5 sec was selected. It can be determined from FIG. 5 that the inspiration time is considerably longer than in FIG. 3, so that more time is left for the gas exchange. The asynchronous activity of the patient, which can be recognized in FIG. 3, is not present in the representation in FIG. 5 because of the use of the process according to the present invention.

Figure 6:
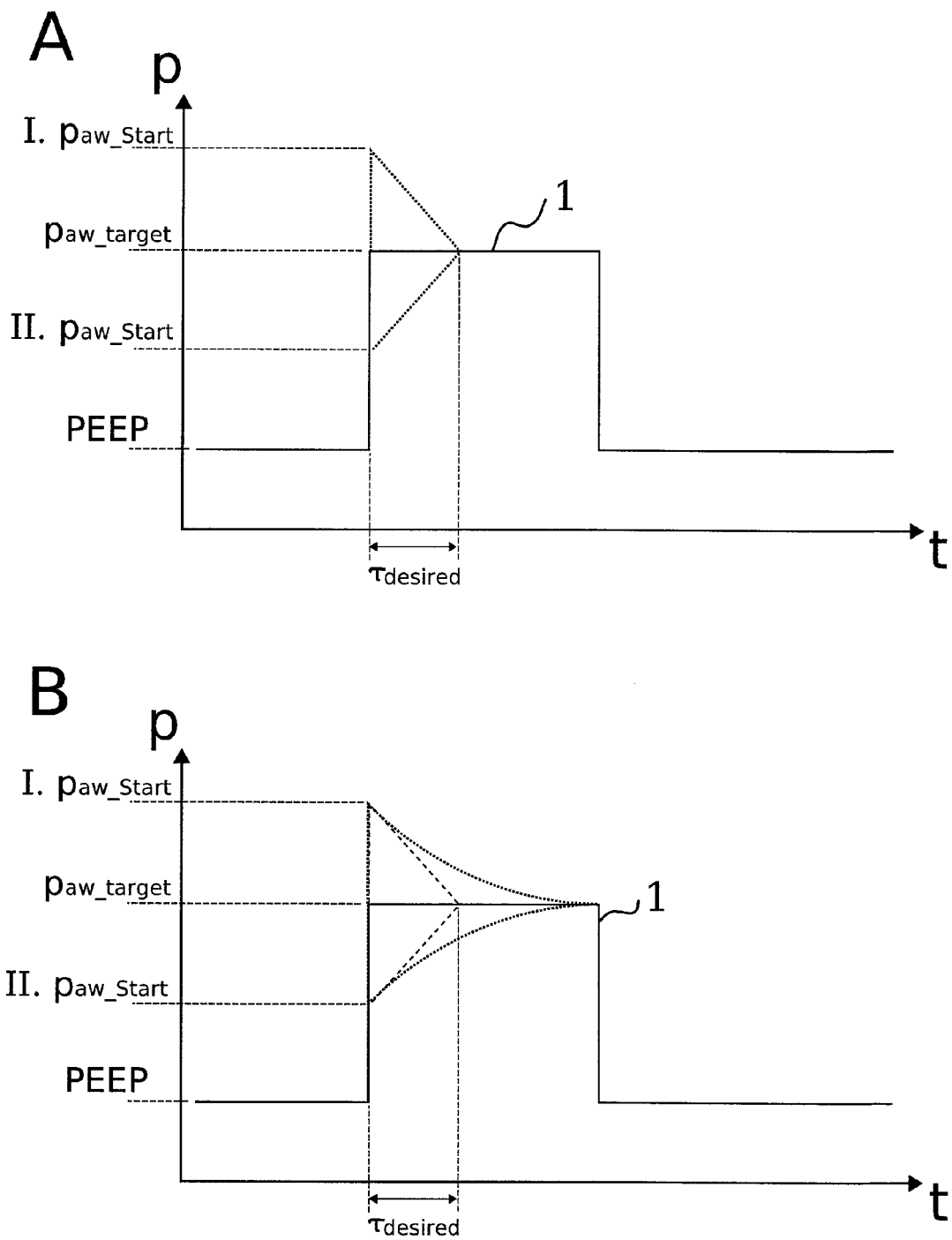
FIG. 6 is a plurality of schematic curves with a ramp-like pressure curve according to the present invention with a linear ramp or pressure curve switching (FIG. 6A) and with an exponential ramp (FIG. 6B)

FIG. 6 shows the schematic curve of the inspiratory pressure switching by means of a linear ramp (FIG. 6A) or an exponential function (FIG. 6B). It can be recognized from FIG. 6A that the starting airway pressure $p_{aw\_Start}$ may be above the airway target pressure $p_{aw\_target}$ (case I), but also below the airway target pressure $p_{aw\_target}$ (case II). The inspiration pressure curve 1 correspondingly rises at the beginning of the duration $\tau_{desired}$ shown at first to $p_{aw\_Start}$ (case I) to drop after the end of the duration $\tau_{desired}$ to the airway target pressure $p_{aw\_target}$, or to rise, in case II, to the airway target pressure $p_{aw\_target}$ over the duration $\tau_{desired}$.

The representation in FIG. 6A describes the linear rise or drop from the starting airway pressure $p_{aw\_Start}$ to the airway target pressure $p_{aw\_target}$. FIG. 6B shows, by contrast, the case in which it assumes the airway target pressure $p_{aw\_target}$ after the rise or drop, following an exponential function. The time constant $\tau_{desired}$ indicates in the representation according to FIG. 6B the time after the end of which a tangent (placed to the inspiration pressure curve 1 at the point in time at which the starting airway pressure $p_{aw\_Start}$ is assumed) intersects the horizontal line at the pressure level of the airway target pressure $p_{aw\_target}$ in the graphic representation.

Figure 7:
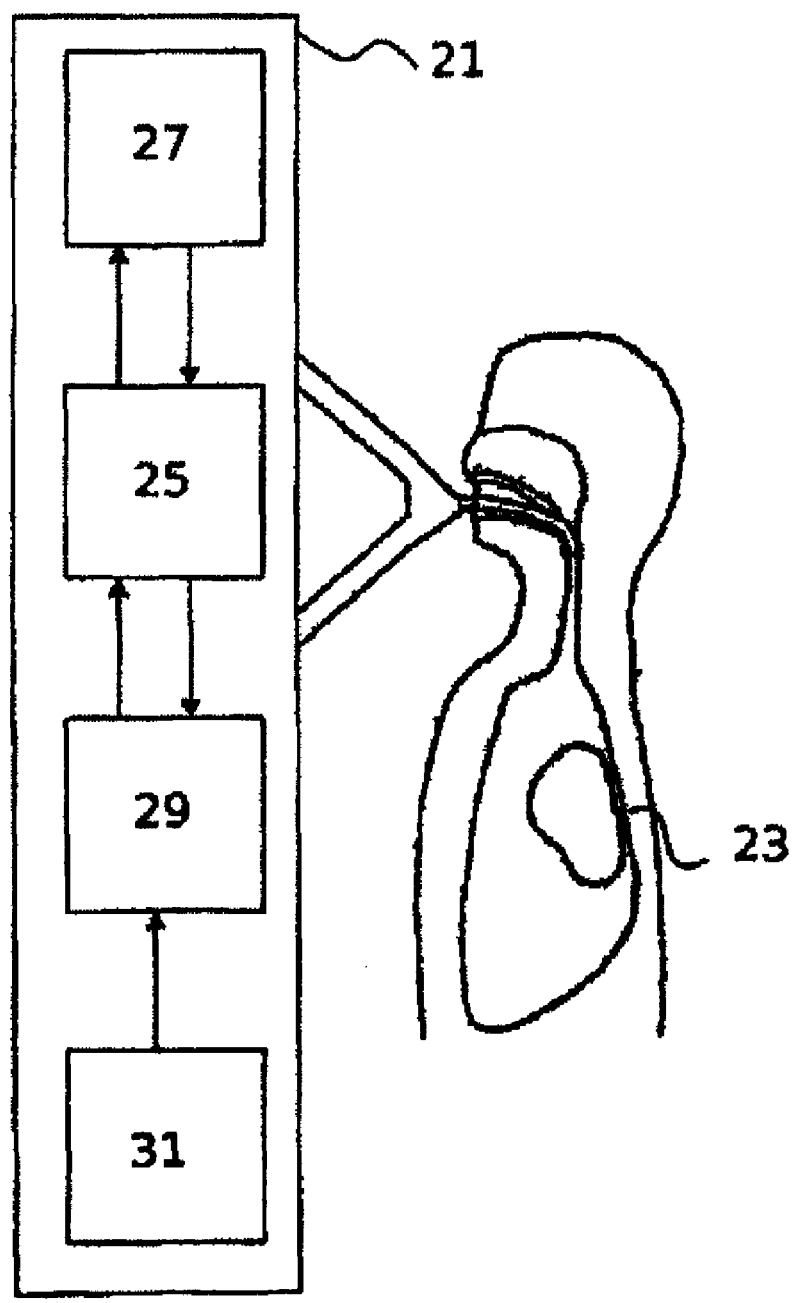
FIG. 7 is a view of a schematically simplified device according to the present invention.

FIG. 7 shows in a schematic and simplified form a respirator 21 according to the present invention for respirating (also known as ventilating) a patient 23. The respirator 21 has a means 25 for shaping the inspiration pressure-vs.-time curve 1. It has, furthermore, a means 27 for setting $\tau_{desired}$ time constant $\tau_{desired}$, a means 29 for determining and/or setting the time constant $\tau$ as well as a means 31 for calculating the ramp-like pressure curve.

In other embodiments, not shown in the figures, the respirator 21 may have a means for determining the time constant $\tau$ of the lung mechanics by means of regression and/or occlusion maneuvers. It may have, furthermore, a means for setting the starting airway pressure $p_{aw\_Start}$, a means for setting a time constant for the rise of the respiration pressure applied, and a means for calculating the ramp-like pressure curve independently from one another. In addition, the device 21 according to the present invention has a means for applying the ramp-like pressure curve.

Thus, a process for operating a respirator with an inspiration pressure-vs.-time curve, which has an airway target pressure and a PEEP, is proposed according to the present invention for the first time ever, in which respirator the inspiration pressure-vs.-time curve reaches the airway target pressure $p_{aw\_target}$ on a ramp-like pressure curve starting from a starting airway pressure $p_{aw\_Start}$ is greater than the PEEP. The present invention proposes, furthermore, a suitable device for carrying out the process according to the present invention.

While specific embodiments of the invention have been shown and described in detail to illustrate the application of the principles of the invention, it will be understood that the invention may be embodied otherwise without departing from such principles.

What is claimed is:

1. A process for operating a respirator with an inspiration pressure-vs.-time curve, which curve has an airway target pressure ($p_{aw\_target}$) and a positive end-expiratory pressure (PEEP), the process comprising the steps of:
   forming the inspiration pressure-vs.-time curve from a starting airway pressure to the airway target pressure ($p_{aw\_target}$) on a ramp-like pressure curve, the starting airway pressure at a beginning of inspiration ($p_{aw\_Start}$) being greater than the PEEP.

2. A process in accordance with claim 1, further comprising:
   shaping the ramp-like pressure curve on a basis of a lung disease of a patient to be respirated.

3. A process in accordance with claim 2, further comprising:
   setting a desired time constant ($\tau_{desired}$) for a time dynamics of a filling of the lungs of the patient;
   determining a time constant ($\tau$) of the lung mechanics of the patient;
   calculating the ramp-like pressure curve based on the desired time constant and the time constant of the lung mechanics.

4. A process in accordance with claim 2, further comprising:
   setting the starting airway pressure ($p_{aw\_Start}$);
   setting a time constant for determining a change over time in the inspiration pressure applied; and
   calculating the ramp-like pressure curve.

5. A process in accordance with claim 1, further comprising:
   setting a desired time constant ($\tau_{desired}$) for a time dynamics of a filling of the lungs of the patient;
   determining a time constant ($\tau$) of the lung mechanics of the patient;
   calculating the ramp-like pressure curve based on the desired time constant and the time constant of the lung mechanics.

6. A process in accordance with claim 5, further comprising:
   determining the time constant ($\tau$) of the lung mechanics by means of regression or occlusion.

7. A process in accordance with claim 3, further comprising:
   setting the time constant ($\tau$) of the lung mechanics on a respirator.

8. A process in accordance with claim 1, further comprising:
   setting the starting airway pressure ($p_{aw\_Start}$);
   setting a time constant for determining a change over time in the inspiration pressure applied; and
   calculating the ramp-like pressure curve.

9. A respirator for applying a inspiration pressure-vs.-time curve which has an airway target pressure ($p_{aw\_target}$) and a positive end-expiratory pressure (PEEP), the respirator comprising:
   means for shaping the inspiration pressure-vs.-time curve, the inspiration pressure-vs.-time curve reaching the airway target pressure ($p_{aw\_target}$) on a ramp-like curve starting from a starting airway pressure ($p_{aw\_Start}$) at a beginning of inspiration, the starting airway pressure ($p_{aw\_Start}$) being greater than the PEEP.

10. A respirator in accordance with claim 9, further comprising:
    means for setting a desired time constant ($\tau_{desired}$) for a time dynamics of a filling of the lungs of the patient;
    means for determining a time constant ($\tau$) of the lung mechanics of the patient;
    means for calculating the ramp-like pressure curve.

11. A respirator in accordance with claim 10, further comprising:
    means for determining the time constant ($\tau$) of the lung mechanics by means of regression and occlusion maneuvers.

12. A respirator in accordance with claim 9, further comprising:
    means for setting the starting airway pressure ($p_{aw\_Start}$);
    means for setting a time constant for determining a change over time in the inspiration pressure applied; and
    means for calculating the ramp-like pressure curve.

13. A process for mechanically ventilating a patient, the process comprising the steps of:
    recording a PEEP (positive end-expiratory pressure) of the patient;
    providing an inspiration pressure/time curve;
    flowing breathing gas into the patient according to the inspiration pressure/time curve, the pressure/time curve transitioning from a starting airway pressure at a beginning of an inspiration stroke to an airway target pressure at an end of the inspiration stoke, the starting airway pressure being higher than the PEEP.

14. A process in accordance with claim 13, further comprising:
    determining a lung disease of the patient;
    shaping the pressure/time curve on a basis of the lung disease of the patient.

15. A process in accordance with claim 13, further comprising:
    setting a desired time constant ($\tau_{desired}$) for filling of the lungs of the patient;
    determining an actual time constant ($\tau$) of the lung mechanics of the patient;

shaping the pressure/time curve on based on the desired and actual time constant.

16. A process in accordance with claim 15, further comprising:
determining the actual time constant (τ) of the lung mechanics by means of one of regression and occlusion.

17. A process in accordance with claim 15, further comprising:
setting the actual time constant (τ) of the lung mechanics on a respirator.

18. A process in accordance with claim 13, wherein:
said inspiration pressure/time curve transitioning from said starting airway pressure to said airway target pressure over a desired time constant, a value of said desired time constant being greater than zero, said value of said desired time constant being selected dependent upon a condition of the lungs of the patient.

19. A process in accordance with claim 18, further comprising:
determining an actual time constant (τ) for filling of the lungs of the patient;
forming said starting airway pressure based on said actual time constant and said desired time constant.

20. A process in accordance with claim 18, further comprising:
determining an actual time constant (τ) of the lungs of the patient;
forming a shape of said inspiration pressure/time curve from said starting airway pressure to said airway target pressure based on said actual time constant and said desired time constant.

* * * * *